United States Patent
Kimoto et al.

(10) Patent No.: US 6,552,074 B2
(45) Date of Patent: Apr. 22, 2003

(54) ARGININE/ASCORBIC ACID MIXED POWDER AS AN ORAL SUPPLEMENT

(75) Inventors: Eiji Kimoto, Jonan-ku (JP); Fukumi Morishige, 2-10-13, Miyakono, Oamishirasato-machi, Sanbu-gun, Chiba-ken (JP)

(73) Assignees: Fukumi Morishige, Sanbu-gun (JP); Sachiko Kimoto, Jonan-ku (JP)

( * ) Notice: Subject to any disclaimer, the term of this patent is extended or adjusted under 35 U.S.C. 154(b) by 0 days.

(21) Appl. No.: 09/987,179

(22) Filed: Nov. 13, 2001

(65) Prior Publication Data
US 2002/0091156 A1 Jul. 11, 2002

(30) Foreign Application Priority Data
Nov. 16, 2000 (JP) ........................................ 2000-349281
Jul. 23, 2001 (JP) ........................................ 2001-221436

(51) Int. Cl.$^7$ ..................... A61K 31/34; A61K 31/195; A01N 45/00
(52) U.S. Cl. ................. 514/474; 514/168; 514/561
(58) Field of Search ................. 514/474, 168, 514/561; 426/533, 590, 656; 424/604, 600, 678, 680

(56) References Cited

U.S. PATENT DOCUMENTS

| | | | | |
|---|---|---|---|---|
| 4,479,974 A | * | 10/1984 | Schenz | 426/590 |
| 4,871,550 A | * | 10/1989 | Millman | 424/601 |
| 4,913,923 A | * | 4/1990 | Van Den Ouweland | 426/533 |

FOREIGN PATENT DOCUMENTS

| | | | | |
|---|---|---|---|---|
| JP | 60066958 A | * | 4/1985 | |
| JP | 60078560 A | * | 5/1985 | |
| JP | 63115821 A | * | 5/1988 | |
| JP | 63115822 A | * | 5/1988 | |

OTHER PUBLICATIONS

Willard J. Visek, "Arginine Needs, Physiological State and Usual Diets. A Reevaluation", Journal of Nutrition, vol. 116, pp. 36–46, 1986.
R. M. J. Palmer et al., "Nitric oxide release accounts for the bioloical activity of endothelium–derived relaxing factor", Nature, vol. 327, pp. 524–526, 1987.
Marian Statter et al., "Competitive Interrelationships Between Lysine And Arginine In Rat Liver Under Normal Conditions And In Experimental Hyperammonemia", Life Sciences, vol. 22, pp. 2097–2102, 1978.
D. Kritchevsky et al., "Atherogenicity of animal and vegetable protein. Influence of the lysine and arginine ratio", Atheroscler., 41, 429–431, 1982.
Adrian Barbul, "Arginine: Biochemistry, Physiology, and Therapeutic Implications", Journal of Parenteral and Enteral Nutrition, vol. 10, pp. 227–238, 1986.
R.C. Rose, "Ascorbic acid protection against free radicals", Ann. N.Y. Acad. Sci., vol. 498, pp. 506–508, 1987.
B. Frei et al., "Ascorbate is an outstanding antioxidant in human blood plasma", Proc. Natl. Acad. Sci. USA, vol. 86, pp. 6377–6381, 1989.
S. S. Mirvish, "Blocking the formation of N–nitroso compounds with ascorbic acid in vitro and in vivo", Ann, N.Y. Acad. Sci., vol. 258, pp. 175–180, 1975.
W.H. Kalus et al., "Inhibition of nitrosamine formation of ascorbic acid: participation of free radicals in its anaerobic reaction with nitrite", Experientia, vol. 36, pp. 147–149, 1980.
Joseph S. Beckman et al., "Pathological implications of nitric oxide, superoxide and peroxynitrite formation", Biochem. Soc. Transact., vol. 21, pp. 330–334, 1993.
G.M. Sobala et al., "Ascorbic acid in the human stomach", Gastroenterol., vol. 97, pp. 357–363, 1989.
Eli Seifter et al., "Arginine: An essential amino acid for injured rats", Surgery, vol. 84, pp. 224–230, 1978.
E. Cameron et al., "Other Properties of Vitamin C", Cancer and Vitamin C, pp. 112, 1979.

* cited by examiner

Primary Examiner—Zohreh Fay
Assistant Examiner—Brian Yong S. Kwon
(74) Attorney, Agent, or Firm—Oliff & Berridge, PLC

(57) ABSTRACT

A mixture obtained by mixing ascorbic acid powder with arginine powder in a weight ratio (ascorbic acid/arginine) of ⅕ to 20, especially ⅕ to ¼; and a supplement such as a nutrient preparation and a health-care food containing the mixture. Mixing of arginine powder and ascorbic acid powder in the weight ratios eliminates stringent taste specific to arginine and alleviates stringent feeling in the stomach (heartburn, nausea or vomiting) after oral intake thereof. The mixture prevents also peroxidative injuries of cells caused by an administration of a great amount of arginine alone. Further, mixing of arginine powder with ascorbic acid powder prevents browning of the mixture after long-term storage.

9 Claims, No Drawings

ARGININE/ASCORBIC ACID MIXED POWDER AS AN ORAL SUPPLEMENT

BACKGROUND OF THE INVENTION

1. Field of the Invention

The present invention relates to a method for eliminating the stringent taste and alleviating stringent feeling in the stomach of L-arginine (hereinafter referred to as arginine) by mixing L-ascorbic acid (hereinafter referred to as ascorbic acid) and for alleviating the toxicity of arginine-derived NO radical by arginine-ascorbic acid-combined treatment.

2. Description of the Related Art

From late 1970's to 1980's, a research group of Illinois University reevaluated that dietary arginine is indispensable for optimal health of adult and especially aged humans. (see E. Kimoto, "Nutritional Chemistry of L-Arginine", Kaisei Publishing Co. Ltd., Tokyo, 1999 (Literature 2), page 93).

In 1987, it was reported that NO radical participating in a wide variety of physiological functions such as blood pressure control and prevention of infections is derived from arginine as a source. This led to increased attention paid to arginine in the field of amino acid nutrition science (see Literature 2, page 57).

Arginine participates in assorted physiological functions. For example, it stimulates detoxication of ammonia via urea cycle, serves as material for the synthesis of creatine phosphate (bioenergy storing form), polyamine (bioactive substance) and proline (an amino acid constituent of collagen), stimulates secretion of endocrine hormones, serves as a source for the production of NO radicals (inter/intra cellular signal transducer) and so forth.

Concerning the nutritional and metabolic aspects of basic amino acids, overabundance of lysine (one of the essential amino acids) and insufficiency of arginine, that is, imbalance of lysine/arginine ratio inhibits antagonistically many of metabolic pathways of arginine, thus can be harmful to health (see Literature 2, page 76).

Furthermore, arginine has been increasingly appreciated not only as a nutrient for average people as collective but also as a "conditionally indispensable" nutrient in order to maintain better health conditions of individuals suffering from some complaint or diseases.

In particular, arginine is an indispensable nutrient for the therapy of post-operative stress or invasion (see Literature 2, page 93).

As described above, alimentation or supplement of arginine is a very useful method for maintaining health. However, arginine and its salt of inorganic acid, such as hydrochloric acid, nitric acid or sulfuric acid have a very stringent taste (harsh, acrid taste, irritating the throat), so that it is very difficult for people to take arginine or the salt. Furthermore, after the intake of arginine or the salt, it often causes stringent feeling in the stomach (heartburn, nausea or vomiting) so that it makes the intake of arginine unpleasant.

Long-term intake of arginine results in increased production of NO gas which changes easily into nitrous acid. A portion of the nitrous acid reacts with dietary-intaken secondary amines to produce carcinogenic nitrosamine compounds. It is well known that ascorbic acid as an antimutagenic vitamin inhibits such a harmful reaction (see, the lower part in the page 10 of Literature 1).

Active oxygen species such as superoxide radical anion ($O_2^{\bullet-}$) are often produced in diseased cells. NO radical readily reacts with $O_2^{\bullet-}$ and produces deleterious peroxynitrite ($O=NOO^-$) (see, the middle part in the page 64 of Literature 2).

SUMMARY OF THE INVENTION

Under the circumstances, the present inventors have made extensive research with a view to solving the problems of difficult intake and unpleasant intake of arginine. As a result, they have found out that mixing arginine powder with ascorbic acid powder and arginine powder in a weight ratio (ascorbic acid/arginine) of ⅕ to ¼ can eliminate the stringent taste of arginine and alleviate the stringent feeling in the stomach (heartburn, nausea, or vomiting). The present invention is based on this discovery.

As far as the present inventors know, a method of mixing arginine powder with ascorbic acid powder in a weight ratio of arginine/ascorbic acid=1:⅕ or more in order to eliminate the stringent taste of arginine is novel. Also, the mixture obtained by this method as well as a supplement containing the mixture is novel.

DETAILED DESCRIPTION OF THE INVENTION

The weight ratio of ascorbic acid used for mixing to arginine is an ascorbic acid/arginine ratio=⅕ to ¼ in the case where a sufficient amount of ascorbic acid to eliminate stringent taste of arginine is to be provided. As the above-mentioned weight ratio is getting smaller than ⅕, the more stringent taste occurs. When the weight ratio is greater than ¼, the acidity of a mixture increases as the above-mentioned weight ratio increases. For example, in the case where the weight ratio is ½, the acidity is considerably strong.

The mixture with the above-mentioned weight ratio of ⅕ to ¼ has also the effects of alleviating the stringent feeling in the stomach after the intake of arginine.

Generally, in the gastric juice of young healthy persons, ascorbic acid is secreted in high concentrations. However, the concentration of ascorbic acid is lowered in the case of chronic gastritis or in the low acid state observed in aged persons (see Literature 1). Also, nitrous acid tends to be generated due to nitrate reduction by bacteria. In this case, too, addition of ascorbic acid is expected to give rise to great effects.

In the therapy of post-operative stress or invasion, both arginine and ascorbic acid are essential nutrient. This is because supply of proline derived from arginine and of hydroxyproline produced by ascorbate-aided oxygenation of proline is essential in the formation of collagen, which is essential for wound healing (see Literature 2, pages 37 to 38). Thus, the mixture of the present invention that contains the both components, i.e., arginine and ascorbic acid is expected to be useful in accelerating the therapy of post-operative stress or invasion.

It is essential that upon and after mixing and ascorbic acid, both components are solid such as powder. The present inventors have studied on mixing aqueous solutions of both components. It is revealed that the obtained mixture undergoes Maillard reaction to turn brow-colored solution disadvantageously with lapse of time. In contrast, it has been found that powder mixture obtained by mixing arginine and ascorbic acid solid undergoes no browning or substantially no browning after standing at room temperature under low humidity for as long as 1 year. The mixture and the supplement according to the present invention are completed based on this discovery.

Each purity of arginine and ascorbic acid solid used in the present invention may be any optional purity ordinarily used in supplements such as nutrient preparations and health-care foods. Usually, used arginine and ascorbic acid solid have purities of 97% or more, respectively.

Arginine and ascorbic acid used for mixing are solid suitable for mixing. And the solid may be powder, fine powder, crystals, micro crystals, or lumps able to be readily ground into fine powders or micro crystals.

Addition of powders of polyol such as xylitol or sorbitol to the above-mentioned mixture is expected to aid preventing the browning from progressing any further.

The mixing is performed usually by mixing arginine and ascorbic acid solid with sufficient grinding so that an uniform powder mixture can be obtained. Usually, mixing is accompanied by pulverization.

Mixing is practiced under low humidity (lower than 40%) in order to avoid as much as possible oxidation of ascorbic acid in humid air.

It is preferred that the material for the inner surface of the grinding device is inert to the components to be mixed and hard, for example, ceramics or earthenware. Examples of the grinding device include highly durable mortar, mill or cylinder (circular cylinder or polygonal cylinder) made of ceramic, for example, earthenware having a smooth or rough inner surface. Since ascorbic acid readily reacts with iron, it is not preferable to use a mill type mixer that cuts and fractures with an iron-made cutter blade.

The mixing is carried out usually at room temperature, preferably 10° C. to 15° C. and with sufficient grinding so that arginine and ascorbic acid can be uniformly mixed.

The mixing time may be selected optionally as far as it is long enough to provide uniform mixture of both components.

The particle size distribution of powder obtained by mixing arginine and ascorbic acid solid ranges from 50, preferably 100, more preferably 200 mesh to smaller sizes.

The mixture may contain an additional component such as vitamins, especially ascorbic acid or components as desired. It may be used in supplements such as nutrient preparation or health-care foods as it is (powder) or after processing into tablets, particles, granules, or capsules.

The optimum intake of ascorbic acid for most people is much higher than the recommended dietary allowance (RDA). Individuals can choose the amount for oral intake necessary to maintain the state of well-being. Thus individuals can choose the amount of ascorbic acid to be added to the mixture or supplement having a weight ratio (ascorbic acid/arginine) of 1/5~1/4.

The upper limit of the ascorbic acid/arginine weight ratio can be determined by a ratio of: {(Upper limit value of usual oral intake amount of ascorbic acid per day)/(lower limit value of usual oral intake amount of arginine per day)}. Thus the upper limit of the weight ratio can be deduced as following:

{(upper limit value of usual oral intake amount of ascorbic acid per day=10 g (in the case of adult weighing about 70 kg))/(lower limit value of usual oral intake amount of arginine per day=0.5 g (in the case of adult weighing about 70 kg))}=20.

The present invention may be practiced in a variety of embodiments, including the following ones.

Embodiment 1

A method for eliminating stringent taste of arginine and alleviating stringent feeling in the stomach after intake of arginine, by mixing ascorbic acid powder in a weight ratio (ascorbic acid/arginine) of 1/5 to 1/4.

Embodiment 2

A mixture for eliminating stringent taste of arginine, comprising arginine powder and ascorbic acid powder in a weight ratio (ascorbic acid/arginine) of 1/5 to 20.

Embodiment 3

A mixture according to Embodiment 2, wherein 1/5 to 20 is 1/5 to 1/4.

Embodiment 4

A supplement comprising a mixture of arginine powder and ascorbic acid powder in a weight ratio (ascorbic acid/arginine) of 1/5 to 20.

Embodiment 5

A supplement according to Embodiment 4, wherein 1/5 to 20 is 1/5 to 1/4.

In the case where the amount of ascorbic acid powder to be added to arginine powder is less than 1/5 times the weight of the arginine powder, the stringent taste of arginine is decreased, and its degree is expected to be proportional to the amount of ascorbic acid powder added. Therefore, in the case where the amount of the ascorbic acid powder is less than 1/5 times the weight of the arginine powder, the following compound that has or is expected to have the effects of eliminating or decreasing stringent taste of arginine may further be added in addition to ascorbic acid. Examples of such a compound include, organic acids, acidic amino acids having two carboxyl groups such as aspartic acid and glutamic acid. In the case where any one of these compounds is added, it is preferred that such an additional compound or compounds should be added taking into consideration additional or synergistic effects with ascorbic acid powder added with respect to the effects of eliminating stringent taste of arginine.

Therefore, the present invention also includes the following embodiments.

Embodiment 6

A mixture for eliminating stringent taste of arginine, comprising arginine powder, ascorbic acid powder and powder of a compound having ability of decreasing or eliminating stringent taste of arginine.

As described above, generally oral intake of arginine induces stringent feeling in the stomach. Mixing arginine powder with ascorbic acid powder in a weight ratio of ascorbic acid/arginine of 1/5 to 1/4 or to 20 results in alleviation of the stringent feeling. Therefore, the present invention also includes the following embodiments.

Embodiment 7

A mixture for alleviating stringent feeling in the stomach after intake of arginine, comprising arginine powder and ascorbic acid powder in a weight ratio (ascorbic acid/arginine) of 1/5 to 20.

Embodiment 8

A mixture according to embodiment 7, wherein 1/5 to 20 is 1/5 to 1/4.

After giving a great amount of arginine (usually in a dose about 1.5 g or more of arginine per day for patients of about 70 kg body weight) to a patient in a peroxidative conditions owing to the formation of a great amount of superoxide radical anion ($O_2^{\bullet-}$) the $O_2^{\bullet-}$ reacts with NO. to give peroxynitrite ion($O=NOO^-$) of extremely high toxicity.

Ascorbate is a typical scavenger of $O_2^{\bullet-}$ and thus could inhibit the production of $O=NOO^-$. In view of the physiological roles of arginine, ascorbate could demonstrate synergistic effects. The inventors have tried this idea for the roles of ascorbate and have discovered that ascorbic acid retards formation of $O=NOO^-$ derived from the reaction of NO. with $O_2 \cdot ^-$ in vitro and in vivo condition. Based on this discovery, an administration of a great amount of arginine combined with ascorbic acid in an amount 1/5 times and more, for example from 1/5 to 20 times, especially from 1.5 to 20 times the amount of the arginine can be expected to prevent peroxidative injuries of cells caused by the ion, O=NOO⁻. Therefore, the present, invention also includes the following embodiments.

Embodiment 9

A mixture for preventing peroxidative injuries of cells caused by an administration of a great amount of arginine, comprising arginine powder and ascorbic acid powder in a weight ratio (ascorbic acid/arginine) of 1/5 to 20.

Embodiment 10

A mixture according to Embodiment 9, wherein 1/5 to 20 is 1.5 to 20.

EXAMPLES

Examination Tests on Strengths of Stringent Taste and Stringent Feeling in the Stomach Six kinds of powder mixtures possessing different ascorbic acid/arginine weight ratios, as shown in Table 1, were prepared by grinding sufficiently in an earthenware motor. Any powder mixture obtained did not show browning with lapse of time at least for one year.

The stringent taste, acidity taste and stringent feeling in the stomach of powder mixtures were consulted by a panel of thirty adult volunteers in total. Each volunteer consulted the tastes and the feeling on one of six different mixtures daily during a week.

TABLE 1

| | Powders mixtures: weight ratio of Ascorbic acid/Arginine | | | | | |
|---|---|---|---|---|---|---|
| | 0.8/5 | 0.9/5 | 1/5 | 1/4 | 1/3 | 1/2 |
| Stringent taste | ++ | + | − | − | − | − |
| Acidity taste | − | − | − | − | + | ++ |

Note: The score ranking of taste felt by more than 20 volunteers among 30 volunteers in total is shown in Table 1.
The scores are based on the following ranking
++: strong stringent taste or acidity
+: slight stringent taste or acidity
−: no stringent taste or acidity The stringent feeling in the stomach after oral intake of 1 g of powder mixture was revealed by several volunteers in case of 0.8/5 ratio, only a few volunteers in case of 0.9/5 ratio, but by none in cases of other ratios.

As will be apparent from the results in Table 1 above, when the weight ratio of ascorbic acid/arginine was 1/5 to 1/4, the stringent taste of arginine disappeared.

The acidity of ascorbic acid was felt when the weight ratio of ascorbic acid/arginine exceeded 1/3. At a weight ratio of 1/2, the acidity of ascorbic acid was strongly felt.

The powder mixture of ascorbic acid/arginine of weight ratio(acid/arginine) 0.8/5 or more can be stored under low humidity without browning with lapse of time at least for one year.

In animal and fish than in vegetable proteins, lysine content is higher relative to arginine content. The protein content of vegetables, however, is very low.

In usual diets in Japan, both arginine content and arginine/lysine ratio are in low levels. Japanese adult people intake only 1~2 g arginine from daily diet on average.

American adult people intake 5.4 g arginine from daily diet on average, who suffer from the imbalance of lysine/arginine ratio. It is well known that lysine is one of the most easily peroxidized amino acids.

Moreover, de novo syntheses of arginine and also serum arginine concentration tend to decrease with ageing.

Long-term daily dietary supplementation with arginine is necessary to prevent age-related diseases and to improve good health.

The powder mixture of ascorbic acid/arginine (weight ratio=1/5~1/4) makes long-term oral intake very easy.

Arginine is one of the least toxic amino acid. Ascorbic acid has also extremely low toxicity. The optimum intake of ascorbic acid for most people is much higher than the recommended dietary allowance. Individuals can choose the amount for oral intake necessary to maintain the state of well-being.

The powder mixture of ascorbic acid/arginine of weight ratio (ascorbic acid/arginine) 0.8/5 or more can be stored under low humidity for long time at least one year without browning.

Literatures

1. Ewan Cameron and Linus Pauling, "Cancer and VitaminC", translated by A. Murata, E. Kimoto, F. Morishige, Kyoritsu Publishing Co. Ltd., Tokyo, 1981.
2. E. Kimoto, "Nutritional Chemistry of L-Arginine", Kaisei Publishing Co. Ltd., Tokyo, 1999.

What is claimed is:

1. A method for eliminating stringent taste of L-arginine and alleviating stringent feeling in the stomach after intake of L-arginine, by mixing L-ascorbic acid powder with L-arginine powder in a weight ratio (L-ascorbic acid/L-arginine) of at least 1/5.

2. A method for eliminating stringent taste of L-arginine and alleviating stringent feeling in the stomach after intake of L-arginine, by mixing L-ascorbic acid powder with L-arginine powder in a weight ratio (L-ascorbic acid//L-arginine) of from 1/5 to 20.

3. A method for eliminating stringent taste of L-arginine and alleviating stringent feeling in the stomach after intake of L-arginine, by mixing L-ascorbic acid powder with L-arginine powder in a weight ratio (L-ascorbic acid/L-arginine) of from 1/5 to 1/4.

4. A waterless supplement for eliminating stringent taste of L-arginine and alleviating stringent feeling in the stomach after intake of L-arginine, consisting essentially of L-arginine powder and L-ascorbic acid powder in a weight ratio (L-ascorbic acid powder/L-arginine) of at least 1/5.

5. A waterless supplement for eliminating stringent taste of L-arginine and alleviating stringent feeling in the stomach after intake of L-arginine, consisting essentially of L-arginine powder and L-ascorbic acid powder in a weight ratio (L-ascorbic acid powder/L-arginine) of from 1/5 to 20.

6. A waterless supplement for eliminating stringent taste of L-arginine and alleviating stringent feeling in the stomach after intake of L-arginine, consisting essentially of L-arginine powder and L-ascorbic acid powder in a weight ratio (L-ascorbic acid powder/L-arginine) of from 1/5 to 1/4.

7. The supplement according to claim 4, wherein the supplement is in the form of a powder.

8. The supplement according to claim 5, wherein the supplement is in the form of a powder.

9. The supplement according to claim 6, wherein the supplement is in the form of a powder.

* * * * *